United States Patent [19]

Templeton

[11] 3,999,973

[45] Dec. 28, 1976

[54] *C. MALVARUM* SPORE CONCENTRATE, FORMULATION, AND AGRICULTURAL PROCESS

[75] Inventor: George E. Templeton, Fayetteville, Ark.

[73] Assignee: The Board of Trustees of the University of Arkansas, Fayetteville, Ark.

[22] Filed: June 19, 1975

[21] Appl. No.: 588,299

[52] U.S. Cl. ........................................ 71/79; 195/81

[51] Int. Cl.$^2$ ............................................ A01N 9/00

[58] Field of Search .......................... 71/79; 195/81

[56] References Cited

UNITED STATES PATENTS 3,849,104 11/1974 Daniel et al. ........................... 71/79

*Primary Examiner*—Joseph Paul Brust

*Attorney, Agent, or Firm*—John J. Killinger; Roman Saliwanchik

[57] ABSTRACT

Preparation of *C. malvarum* spores, spore concentrates and agricultural formulations for use as a mycoherbicide by application onto undesired vegetation; e.g., teaweed or to the situs of the undesirable vegetation, controlling the undesired vegetation in cropland and other locales where the presence of the vegetation is undesired.

3 Claims, No Drawings

C. MALVARUM SPORE CONCENTRATE, FORMULATION, AND AGRICULTURAL PROCESS

BRIEF SUMMARY OF THE INVENTION

This invention relates to the commercial growing of C. malvarum and collecting of the spores therefrom, concentrating the spores and formulating the spores in a formulation adapted for distributing over geographical locales or a situs where the spores germinate and give rise to a pathogenic disease in undesirable vegetation, thereby controlling the vegetation.

DETAILED DESCRIPTION OF THE INVENTION

Prickley sida (Sida spinosa L.) or teaweed is causing increasing concern to cotton and soybean farmers. It is widely distributed and is a pest throughout the eastern two-thirds of the country. This broadleaf weed occurs in waste places, cultivated fields, open ground, gardens, and pastures.

Sida is not controlled by the more popular chemical herbicides widely used for grassy weed control in pest management systems for cotton and soybeans. This probably accounts for its rise in importance as most grassy weeds are being increasingly controlled.

Development of chemicals for control of sida in cotton fields is complicated by its relatively close relationship to cotton. Both are members of the mallow family (Malvaceae), thus placing unusually stringent specificity requirements on potential chemicals for herbicidal use.

There are, however, serious inadequacies of present chemical weed control systems. Chemicals frequently fail to give residual weed control. Weed seeds that lie dormant in the soil may germinate after chemical treatments, grow and compete with the crop or require repeated treatments for control. Chemicals frequently injure the crop significantly, yet are widely used because removal of weed competition provides economical returns. This injury to the crop greatly increases the risk of serious plant disease epidemics in the injured crop that are normally insignificant in an uninjured crop. Chemicals frequently injure non-target crops by drift of spray droplets or dust particles to sensitive plant species in neighboring fields. Chemicals may injure wildlife, fish, shellfish, or other important animal elements of the environment. Chemicals may have undesirable residues in the crop or soil that would affect consumers of the final products or buildup in food chains in the environment to deleterious levels. Chemicals sometimes interact unfavorably with fertilizer or other pesticides, becoming ineffective or result in damage to the crop.

Furthermore, many potential chemical herbicides would persist in the environment as harmful residues in the harvested crop, or in the soil to harm succeeding crops or to biomagnify in food chains. In soybeans, especially economic and energy conservation argues for an alternative to chemical weed control.

This invention relates to a novel alternative for controlling the weed which is the use of a fungus that is pathogenic to teaweed.

The fungus is Colletotrichum malvarum (A. Braun and Casp) Southworth. It produces a relatively insignificant stem spot disease on the weeds as they approach maturity, yet causes a devastating seedling blight of young weed seedlings. This group of organisms has a small percentage of seed-borne infection, and thus there is probably a low percentage of infected seeds.

The organism, C. malvarum, has been deposited and can be obtained from the permanent collection of the Fermentation Division, Northern Utilization Researth Branch, U.S. Department of Agriculture, Peoria, Illinois, where it has been deposited under an unrestricted deposit as C. malvarum NRRL 8096.

The fungus, C. malvarum, is pathogenic to teaweed (prickley sida, spring sida) Sida spinosa L.; Velvet leaf, Abutilon theophrastii Medic.; Hollyhock, Althea rosea (L.) Cov.; Tree mallows, Lavatera spp.; and Mallow, noncultivated species. Malva nicaeensis All., M. parvifloro L.; and M. rotundifolia L.

The organism, C. malvarum produces typical anthracnose lesions with abundant sporulation from pustules (ascurvuli) scattered throughout the lesion. On leaves and stems of mature plants these lesions range in size from 0.5 to 2 cm. in length, sometimes coalesce, and frequency develop at the leaf axil. The ascervuli are setose and slightly sunken in the host tissue. In moist conditions, flesh colored slimy masses of spores accumulate on the upper surface of the ascervulus breaking the epidermal layer and cuticle. Spores (conidia) are cylindrical with apices rounded, and range in size from 4.8 to 5.5 microns by 11.4 to 12.4 microns and average 5.2 to 12 microns. Setae are dark brown to black, abundant, once or twice septate 2.5 to 5 micron wide at the base and 35–60 microns long and tapered towards the tip.

C. malvarum can be grown on solid or in liquid media for spore production. Solid media can be, for example, (1) water agar, (2) potato dextrose agar (Difco), (3) lima bean agar (Difco), (4) corn meal agar (Difco), (5) potato-carrot agar (Tuite 19), and (6) teaweed agar (blend 10 grams teaweed tissue in 1000 ml. water and solidify with 20 grams agar).

For large scale production in fermentation tanks, liquid media is used, for example:

| Formula I - Modified Richard's Solution - V-8* | | |
|---|---|---|
| Sucrose | 50 | gm. |
| Potassium Nitrate | 10 | gm. |
| Potassium Phosphate, Monobasic | 5.0 | gm. |
| Magnesium Sulfate.7H$_2$O | 2.50 | gm. |
| Ferric Chloride | .02 | gm. |
| V-8 juice | 15 | ml. |
| Distilled water to make | 1000 | ml. |

*Trademark, The Campbell Soup Company for mixed vegetable juices.

Formula II — Modified Richard's Solution — Distillers Solubles

Same as Formula I but substitute 15 gm. Distillers solubles for V-8 juice.

Formula III — Modified Richard's Solution — Brewers Yeast

Same as Formula I above but substitute 15 grams brewers yeast for V-8 juice.

Formula IV — Modified Richard's Solution — Torula Yeast

Same as Formula I above but substitute 16 gm. torula yeast for V-8 juice.

Formula V — Oatmeal Solution — 2%

20 Grams oatmeal blended in 1000 ml. distilled water.

Formula VI — Oatmeal Solution — 4% + 2% sugar 40 grams oatmeal
20 grams sucrose 1000 ml. distilled water The fermentation is commenced in preseed liter flasks containing about 300 ml. of liquid media which has been inoculated with spores. The media is incubated for 1 to 3 days, 2 days preferred, in a closed system with agitation at ambient temperature, preferably from 26° to 30° C.

The preseed is then transferred aseptically to twenty liter seed tanks with additional sterile liquid media. The tanks are provided with air flow and agitation. The fermentation is continued at ambient temperature for 1 to 3 days, 2 days preferred.

250 Liter fermentors are aseptically inoculated from the seed tanks, additional sterile fermentation media added, pH adjusted to 6, supplied with air and agitation and fermented at ambient temperature for from 1 to 3 days, 2 days preferred.

The contents of the fermentation tanks are filtered to remove solids and the mycelium. The filtered beer is then centrifuged. The supernate is discarded and the spore concentrate resuspended in water and recentrifuged. The supernate again discarded and the spore concentrate is collected, placed in plastic bags and stored in ice. The concentrate so stored maintains an 80% germination for up to 21 days.

The spore concentrate is mixed with an agriculturally acceptable diluent or carrier for application to the undesired host vegetation or a situs. By the term "situs" is meant these areas infested with the undesired vegetation or are potential infestation sites.

The preferred carrier is water, and the spore concentrate is dispersed to make a concentration of from about $1 \times 10^6$ to $1 \times 10^9$ spores/ml. The formulation is then sprayed on the undesired vegetation or situs by conventional spraying equipment or from the air in an amount of from about 50 to 500 liters per hectare.

*C. malvarum* does not infect cotton, barley, rye, soybeans, corn, grain sorghum, leguminous vegetable crops, peas, green beans and can be used in these and other fields for weed control.

It is preferred that the application be made when the undesired vegetation has just emerged, e.g., 14 days post-emergence although the application can also be done before emergence.

EXAMPLE 1

A. Inoculum

Spores of *C. malvarum* are inoculated on slants of malt agar. The organism sporulates within 5 days.

B. Preseed

One liter flasks (closed system) with 300 ml. of sterilized Modified Richard's solution — V-8 with pH adjusted to 6 are inoculated with 5 ml. from a washed slant. The closed system is incubated for 72 hours on a 270 rpm rotary shaker at 28° C. for 48 hours.

C. Seed

Twenty liter seed tanks containing 20 liter of Modified Richard's Solution — V-8 are inoculated with 300 ml of preseed and incubated for 48 hours at 28° C. with an agitation speed of 200 rpm and an air flow rate of 10 slm with 10 psig back pressure. Ucon* at 0.5 ml./l. is used to control foam.

* Silicon defoaming agent.

D. Fermentation

Two 250 liter fermentors are inoculated with 25 liters of seed. Agitator speed is fixed at 200 rmp. Air flow is adjusted to 100 slm with 10 psig back pressure. Ucon is added automatically as a defoaming agent.

The pH is controlled at about 6.7 with sulfuric acid. Fermentation is continued for 48 hours at 28° C.

E. Isolation

The fermentation beer is passed through a 48 inch dia. × 150 mesh vibrating screen to remove particles. The spores are removed from the screened beer by running through two Sharples "presurtite" centrifuges. The centrifuges are fed in parallel at 3.5 liters/minute. The supernatant is discarded.

The solids (spores) are washed by reslurrying in 80 liters of water and recentrifuged. The supernatant is discarded and the wet solids (spore concentrate) containing $1.5-2 \times 10^9$ spores/gram are packed in plastic bags in an ice chest.

F. Application

The spore concentrate is mixed with water to a concentration of $2 \times 10^6$ spores/ml. and sprayed at the rate of 94 liters per hectare of cotton field infested with teaweed. The spray is applied when the teaweed is 8 to 10 centimeters tall (approximately 14 days post-emergence). Symptoms of the disease appear on the weed about 7–10 days after application and the weed dies in 12–14 days.

The fungus sporulates on the dead weed tissue and is spread to other emerging weeds by splashing rain, wind, or insects, thereby giving residual control.

EXAMPLE 2

Following the procedure of the preceding Example 1, spores are similarly prepared and sprayed on cotton, barley, rye, soybean, corn, grain sorghum, pea, or green bean fields for control of undesired vegetation, particularly teaweed.

I claim:

1. A composition for agricultural application for controlling undesirable vegetation comprising *Colletotrichum malvarum* spores in association with an agricultural carrier having a spore concentration of from about $1 \times 10^6$ spores/ml. of carrier to about $1 \times 10^9$ spores/ml. of carrier.

2. A process for controlling undesirable vegetation comprising the application of *Colletotrichum malvarum* spores onto the undesired vegetation or onto the situs of the undesired vegetation.

3. The process of claim 2 wherein the undesired vegetation is *Sida spinosa* L.

* * * * *